United States Patent [19]

Cantu

[11] Patent Number: 4,465,068
[45] Date of Patent: Aug. 14, 1984

[54] METALLIC AID AND TECHNIQUE IN FITTING VOICE PROSTHESIS

[75] Inventor: Evangeline Cantu, San Antonio, Tex.

[73] Assignee: The United States of America as represented by the Secretary of the Air Force, Washington, D.C.

[21] Appl. No.: 394,945

[22] Filed: Jul. 2, 1982

[51] Int. Cl.³ .......................... A61B 17/00; A61F 1/20
[52] U.S. Cl. ................................... 128/303 R; 3/1.3; 128/200.26
[58] Field of Search ........... 3/1.3; 128/200.26, 207.14, 128/207.15, 207.16, 207.17, 303 R, 305.3; 604/170

[56] References Cited

U.S. PATENT DOCUMENTS

| | | | |
|---|---|---|---|
| 2,923,299 | 2/1960 | Blackwood | 128/207.17 |
| 3,263,684 | 8/1966 | Bolton | 128/207.16 |
| 3,395,711 | 8/1968 | Plzak, Jr. | 128/200.26 |
| 3,556,103 | 1/1971 | Calhoun et al. | 128/200.26 |
| 3,704,707 | 12/1972 | Halloran | 128/92 EB |
| 3,885,561 | 5/1975 | Cami | 128/214 |
| 4,190,057 | 2/1980 | Hill et al. | 128/675 |
| 4,202,349 | 5/1980 | Jones | 128/689 |
| 4,223,411 | 9/1980 | Schoendorfer et al. | 3/1.3 |
| 4,294,260 | 10/1981 | Veatch | 128/654 |

FOREIGN PATENT DOCUMENTS

| | | | |
|---|---|---|---|
| 529404 | 11/1940 | United Kingdom | 128/200.26 |
| 2077109 | 12/1981 | United Kingdom | 3/1.3 |

OTHER PUBLICATIONS

Eye, Ear, Nose & Throat Catalogue, V. Mueller & Co., Chicago, 1929, pp. 232–233.
Vitallium Surgical Appliances and Instruments (Catalog), Austenal Company, Surgical Products, Division of Howe Sound Company, 1964, captioned page "What Is Vitallium?".
Mark I. Singer, "An Endoscopic Technique for Restoration of Voice After Laryngectomy", Apr. 14–15, 1980, pp. 529–533.

Primary Examiner—Ronald L. Frinks
Attorney, Agent, or Firm—Donald J. Singer; Bobby D. Scearce

[57] ABSTRACT

A metallic insert for use in radiographically fitting a voice prosthesis to a post-laryngectomy patient is described which comprises an elongate, generally cylindrically shaped cast metal member sized to fit snugly within the housing of a dummy prosthesis whereby the fit of the prosthesis can be accurately assessed radiographically in minimum time and with optimal fit to the individual patient.

7 Claims, 2 Drawing Figures

METALLIC AID AND TECHNIQUE IN FITTING VOICE PROSTHESIS

RIGHTS OF THE GOVERNMENT

The invention described herein may be manufactured and used by or for the Government of the United States for all governmental purposes without the payment of any royalty.

BACKGROUND OF THE INVENTION

This invention relates generally to devices and techniques for fitting prosthetic devices, and more particularly to an insert for fitting prosthetic voice devices to post laryngectomy patients.

In the restoration of voice capability to a patient following a laryngectomy, a widely used and accepted technique for prosthetic fitting is the tracheoesophageal puncture procedure, followed by the fitting of a valved voice prosthesis, such as described by Singer and Blom (Ref: Mark I. Singer and Eric D. Blom, "An Endoscopic Technique for Restoration of Voice After Laryngectomy", Ann. Otol. 89:529 (1980)). The clinical fitting of the voice prosthesis, such as the Blom-Singer device, is often hindered by the inability to view the device in place and consequently to size the device and position it within the trachea of the patient for optimal operation and minimal interference with tracheal and esophageal functions.

The present invention provides a novel metallic insert for fitting a prosthetic voice device for a post laryngectomy patient. The technique disclosed allows improved radiographic visualization of the voice prosthesis in place, which results in quicker, simpler and more accurate sizing and fitting of the prosthesis to the patient. Radiographic assessment of the prosthesis fit may be accomplished in as little as ten minutes, as compared to about one hour using existing fitting procedures, and without regard to variations in cervical area tissue thickness or density of a patient.

It is, therefore, an object of the present invention to provide a device for fitting a voice prosthesis to a post-laryngectomy patient.

It is a further object of the present invention to provide a quick, simple, and accurate fitting technique for a voice prosthesis.

These and other objects of the present invention will become apparent as the detailed description of representative embodiments thereof proceeds.

SUMMARY OF THE INVENTION

In accordance with the foregoing principles and objects of the present invention, a metallic insert for use in radiographically fitting a voice prosthesis to a post-laryngectomy patient is described which comprises an elongate, generally cylindrically shaped cast metal member sized to fit snugly within the housing of a dummy prosthesis whereby the fit of the prosthesis can be accurately assessed radiographically in minimum time and with optimal fit to the individual patient.

DESCRIPTION OF THE DRAWINGS

The present invention will be more clearly understood from the following detailed description of representative embodiments thereof read in conjunction with the accompanying drawings wherein.

DETAILED DESCRIPTION

Figure 1:
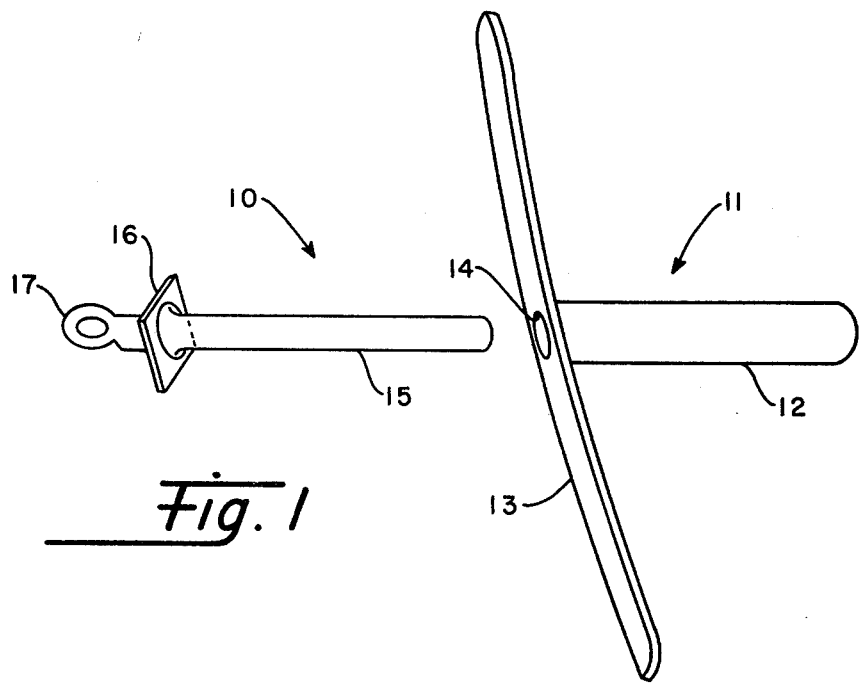
FIG. 1 is a perspective view of the insert of the present invention near a dummy prosthesis inside which the insert is configured to fit.

Referring now to FIG. 1, the novel radio-opaque insert 10 of the present invention is shown withdrawn from its mating dummy prosthesis 11. Post-laryngectomy patients who have experienced the tracheoesophageal puncture procedure may be fitted with a voice prosthesis of the general design of which dummy prosthesis 11 is representative, viz., the Blom-Singer device referenced above. Dummy prosthesis 11 comprises a hollow, generally cylindrical housing portion 12 of silicone having a retention flange 13 attached thereto, and otherwise comprises a replica of the housing of an operable voice prosthesis. These devices are normally available in lengths (of cylindrical portion 12) of 2.2, 2.6., 3.0, 3.3., 3.6, 4.0 and 4.3 cm, and have an outer diameter of 0.5 cm. Dummy prosthesis 11 has an opening 14 at the flange 13 end thereof.

The metallic insert 10 of the present invention may comprise any of a wide range of readily castable metals which are substantially opaque radiographically. The insert 10 fabricated in demonstration of the invention herein comprised a chromium-cobalt alloy. As shown in FIG. 1, the insert 10 includes an elongate, generally cylindrical body portion 15 having a length, diameter and surface contour conforming to the internal configuration of dummy prosthesis 11. Insert 10 may desirably include a flange 16 for facilitating positioning within dummy prosthesis 11, and an attaching ring 17 for facilitating the safe handling thereof during a fitting procedure.

In the fabrication of an embodiment of the novel insert 10 of the present invention, according to a preferred representative procedure, an appropriate length of round wax pattern was inserted into the dummy prosthesis and cut slightly (about 0.5 mm) longer than the internal length thereof in order to form a wax pattern of the internal contour of the prosthesis. A small (5×5 mm) piece of the casting wax was then luted to the end of the wax rod, and an investment casting mold of the pattern was made. A metal casting was then made, removed from the mold, and sand blasted and polished conventionally to the desired surface finish to form the completed insert 10 having an outer contour matching the internal surface contour of dummy prosthesis 11. A series of inserts 10 may be sized and fabricated as described to fit the corresponding sizes of available prostheses as discussed above. The various sizes of inserts 10 may then be reuseable for a plurality of fittings according to the particular patient's needs.

Figure 2:
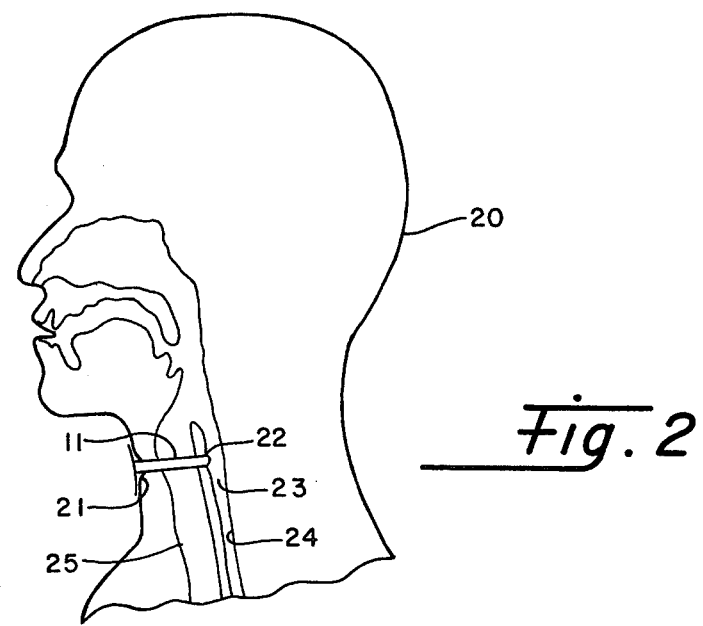
FIG. 2 is a schematic representation of a lateral radiographic view of the tracheoesophageal region of a patient showing placement of a dummy prosthesis and insert.

In the fitting of a prosthesis of the Blom-Singer type, subjective fitting is first performed by the otolaryngologist and speech pathologist according to an individual patient's needs. As shown in FIG. 2, the insert 10 of the present invention may allow exact placement of the prosthesis, and verification of the correct sizing of the prosthesis to an individual patient. As shown in FIG. 2, patient 20 has experienced a laryngectomy and has been provided with a tracheoesophageal stoma 21 preparatory to fitting of a voice prosthesis. A dummy prosthesis 11 may then be inserted into the tracheoesophageal puncture tract 22. Optimal fit is achieved when the dummy prosthesis 11 spans the tracheal lumen 25 and stents the puncture tract 22 with the rounded tip end of dummy prosthesis 11 minimally extending into the esophageal lumen 23, substantially as shown. Excess length or overfitting of prosthesis 11 may result in undesirable impingement against the posterior esophageal wall 24 with attendant esophageal obstruction, tissue irritation decreased air flow or impaired speech production. Insufficient length or underfitting may result in partial stenosis of tract 22 with loss of voice production capability.

Radiographic evaluation of the dummy prosthesis 11 is hindered by the inability to visualize the prosthesis through the tissues of the lower neck and upper thorax on a true lateral view. Proper fitting, evaluation and placement of a prosthesis may be performed by inserting the insert 10 into the dummy prosthesis 11 in place in tract 22, as shown in FIG. 2. Radiographic evaluation in the true lateral view of patient 20, substantially as shown schematically in FIG. 2, may then be made utilizing fluoroscopy during swallowing by patient 20 of a barium suspension or the like in order to verify proper fit of the prosthesis.

The present invention, as hereinabove described, therefore provides an aid for fitting a voice prosthesis to a patient following a laryngectomy characterized by improved radiographic visibility and simplification of the fitting procedure for the prosthesis. It is understood that certain modifications to the invention as hereinabove described may be made, as might occur to one with skill in the field of this invention, within the scope of the appended claims. Therefore, all embodiments contemplated hereunder have not been shown in complete detail. Other embodiments may be developed without departing from the spirit of this invention or from the scope of the appended claims.

I claim:

1. A device for fitting a voice prosthesis to a post-laryngectomy patient having a tracheostoma for receiving said prosthesis, comprising:
   a. a hollow, generally tubular housing, conforming in outer surface contour to taht of said prosthesis, for insertion into said tracheostoma;
   b. a solid, substantially radiographically opaque, generally cylindrical metallic member having a body portion of outer surface contour conforming to the inner surface contour of said housing and insertable into said housing; and
   c. means for positioning said member and said housing within the trachea of said patient for viewing using radiographic means.

2. The device as recited in claim 1 wherein said positioning means includes a flange on one end of said metallic member for aligning said member within said housing.

3. The device as recited in claim 2 further comprising a retaining ring on the flange end of said metallic member.

4. The device as recited in claim 1 wherein said metallic member comprises cast chromium-cobalt alloy.

5. A technique for fitting a voice prosthesis to a post-laryngectomy patient having a trachemostoma for receiving said prosthesis, comprising the steps of:
   a. providing a hollow, generally tubular housing, conforming in outer surface contour to that of said prosthesis;
   b. inserting said housing into said tracheostoma;
   c. providing a solid, substantially radiographically opaque, generally cylindrical metallic member having a body portion of outer surface contour conforming to the inner surface contour of said housing;
   d. inserting said member into said housing; and
   e. determining the position of said housing and said member within the trachea of said patient using radiographic means.

6. The technique as recited in claim 5 wherein said member includes a flange on one end thereof for aligning said member and housing within said trachea.

7. The technique as recited in claim 5 wherein said metallic member comprises cast chromium-cobalt alloy.

* * * * *